United States Patent [19]

Pfirmann et al.

[11] Patent Number: 5,739,388
[45] Date of Patent: Apr. 14, 1998

[54] PROCESS FOR THE PREPARATION OF AROMATIC COMPOUNDS BY DECARBOXYLATION OF AROMATIC CARBOXYLIC ACIDS

[75] Inventors: Ralf Pfirmann, Griesheim; Hans Schubert, Kelkheim, both of Germany

[73] Assignee: Hoechst Aktiengesellschaft, Germany

[21] Appl. No.: 641,877

[22] Filed: May 2, 1996

[30] Foreign Application Priority Data

May 2, 1995 [DE] Germany ............... 195 15 985.3

[51] Int. Cl.⁶ ........................... C07C 51/38
[52] U.S. Cl. .................. 562/479; 562/474; 570/127
[58] Field of Search .................. 570/142, 127; 562/474, 479

[56] References Cited

U.S. PATENT DOCUMENTS 5,329,054  7/1994  Theriot ................... 570/142

FOREIGN PATENT DOCUMENTS 0635466  1/1995  European Pat. Off. .
818434  8/1959  United Kingdom .

*Primary Examiner*—Samuel Barts
*Attorney, Agent, or Firm*—Connolly and Hutz

[57] ABSTRACT

The present invention relates to a process for the preparation of compounds of the formula

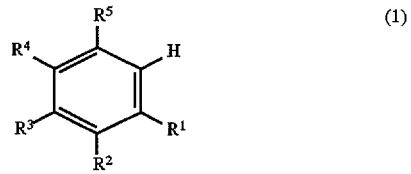

(1)

in which the radicals $R^1$, $R^2$, $R^3$, $R^4$ and $R^5$ are identical or different and are COOH, H, F, Cl, Br, $CF_3$, OH, an alkoxy or alkyl radical having in each case 1 to 4 carbon atoms or a radical $-NR^6R^7$, in which $R^6$ and $R^7$ are identical or different and are H, an alkyl radical having 1 to 4 carbon atoms or a phenyl radical, by dissolving in water a compound of the formula

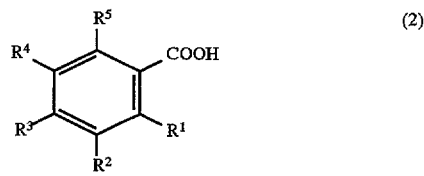

(2)

in which the radicals $R^1$, $R^2$, $R^3$, $R^4$ and $R^5$ are identical or different and have the abovementioned meaning or, in departure therefrom, instead of H can be COOH, admixing the aqueous solution with a water-insoluble amine which is inert under the reaction conditions and carrying out the decarboxylation at a pH of 3 to 9 and a temperature of 70° to 210° C. in the presence or absence of a water-insoluble solvent which is inert under the reaction conditions and in the presence or absence of a decarboxylation catalyst.

32 Claims, No Drawings

PROCESS FOR THE PREPARATION OF AROMATIC COMPOUNDS BY DECARBOXYLATION OF AROMATIC CARBOXYLIC ACIDS

The present invention relates to a process which is improved in comparison to the prior art for the preparation of aromatic compounds, in particular aromatic carboxylic acids, by decarboxylation of corresponding aromatic carboxylic acids, in particular phthalic acids.

Aromatic compounds and aromatic carboxylic acids, in particular fluorinated aromatic carboxylic acids, are valuable intermediates for the preparation of antibacterial agents (DE-A 33 18 145, EP 0 424 850, EP 0 271 275), but they can also be used for the preparation of liquid crystal materials (EP 0 602 596).

As can be shown by the example of the preparation of 2,3,4,5-tetrafluorobenzoic acid by decarboxylation of tetrafluorophthalic acid, there has been no lack of attempts in the past to prepare fluorinated aromatic carboxylic acids by decarboxylation of corresponding phthalic acids.

DE-A 38 10 093 describes the preparation of tetrafluorobenzoyl chloride by decarboxylation of tetrafluorophthalic acid which is dissolved in an excess of quinoline. After the reaction is completed, a quinoline salt of tetrafluorobenzoic acid is obtained, which is then suspended in thionyl chloride and reacted with heating. The 2,3,4,5-tetrafluorobenzoyl chloride is then obtained by fractional distillation (cf. also Example 4).

EP 0 218 111 describes a process for the preparation of 2,3,4,5-tetrafluorobenzoic acid, tetrafluorophthalic acid being dissolved in a polar aprotic solvent and decarboxylated with the use of an organic amine as catalyst. As follows from Examples 1 and 2 with the use of dimethyl sulfoxide as polar, aprotic solvent and triethylamine as organic amine, on the one hand the polar aprotic solvent is used in a great excess and, on the other hand, the actual decarboxylation is followed by a complicated workup proceeding via a plurality of stages. The mixture is first cooled using ice, a large amount of deionized water is added to the reaction mixture and n-butyl ether and toluene are then added. Concentrated sulfuric acid is then added carefully with stirring and cooling, the phases are separated and the aqueous phase is extracted twice with toluene. The organic phases are combined and then extracted three times with 2% strength aqueous sulfuric acid. The organic phase is then dried over anhydrous sodium sulfate, filtered and the filtrate is concentrated under reduced pressure, a solid (2,3,4,5-tetrafluorobenzoic acid) being obtained.

A process using tertiary amines, analogous to the process of EP 0 218 111, is described in JP 63 295 529. 3,4,5,6-Tetrafluorophthalic acid is dissolved in tributylamine and the decarboxylation is carried out in this solution at 130° C. Workup of the reaction mixture produced in this process would, because of the similarity of tributylamine to triethylamine, require an expenditure just as great as described above in EP 0 218 111.

EP 0 194 671 relates to a process for the preparation of 2,3,4,5-tetrafluorobenzoic acid by decarboxylation of 3,4,5,6-tetrafluorophthalic acid in an aqueous medium adjusted to a pH range of 0.7 to 2.2. It is expressly noted on page 3, lines 29 to 33, that the selectivity of decarboxylation in the direction of 2,3,4,5-tetrafluorobenzoic acid is inadequate if the pH of the aqueous medium deviates from said range. The reaction requires, as can be taken from the examples, relatively high temperatures of 155° to 170° C. The use of a relatively large amount of catalyst, that is 0.3 mol of $(NH_4)_2SO_4$ and 0.8 mol of quinoline per mole of tetrafluorophthalic acid leads, at a reaction temperature of 160° C. and a reaction time of 18 hours, to a yield of 88.8% of 2,3,4,5-tetrafluorobenzoic acid (cf. Example 12 in Table 1).

Disadvantages of the process are, on the one hand, the relatively high reaction temperatures and, on the other hand, the relatively long reaction times. Furthermore, because of the low pH of the aqueous solution which is established by the concentration of the 3,4,5,6-tetrafluorophthalic acid dissolved in water, considerable problems are produced with respect to corrosion, caused by the reaction at high temperatures of aqueous corrosive solutions of this type.

With regard to the disadvantages of the above described processes of the prior art, the object is to develop a process which, on the one hand is not restricted only to the preparation of 2,3,4,5-tetrafluorobenzoic acid by decarboxylation of 3,4,5,6-tetrafluorophthalic acid, but can also be applied in greater scope to other carboxylic acids, and, on the other hand, avoids the disadvantages of the above described processes, for example the complicated workup of the resulting reaction mixture, the employment of high temperatures and long reaction times and the use of corrosive aqueous solutions. Furthermore, the process is to be able to be carried out without great expenditure in terms of equipment in a simple manner and, in addition, is to start from relatively readily accessible starting materials and auxiliaries.

This object is achieved by a process for the preparation of compounds of the formula

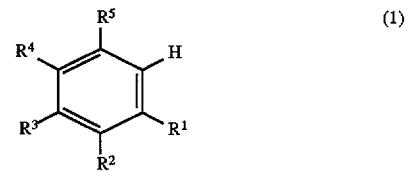

(1)

in which the radicals $R^1$, $R^2$, $R^3$, $R^4$ and $R^5$ are identical or different and are COOH, H, F, Cl, Br, $CF_3$, OH, an alkoxy or alkyl radical having in each case 1 to 4 carbon atoms or a radical $-NR^6R^7$, in which $R^6$ and $R^7$ are identical or different and are H, an alkyl radical having 1 to 4 carbon atoms or a phenyl radical. It comprises dissolving in water a compound of the formula

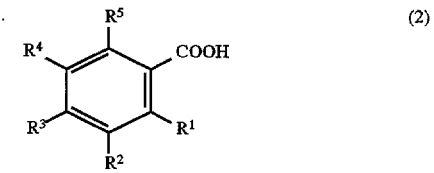

(2)

in which the radicals $R^1$, $R^2$, $R^3$, $R^4$ and $R^5$ are identical or different and have the abovementioned meaning or, in departure therefrom, instead of H can be COOH, admixing the aqueous solution with a water-insoluble amine which is inert under the reaction conditions and carrying out the decarboxylation at a pH of 3 to 9 and a temperature of 70° to 210° C. in the presence or absence of a water-insoluble solvent which is inert under the reaction conditions and in the presence or absence of a decarboxylation catalyst.

The process of the invention is not restricted to the decarboxylation of a single COOH group. It may also be applied to the decarboxylation of two or more COOH groups, in which case, in these cases, the radicals $R^1$, $R^2$, $R^3$, $R^4$ and $R^5$ are identical or different and, in departure from the meaning mentioned in the compound of formula (1), instead of H are COOH. The elimination of $CO_2$ forms, from the COOH group of the starting material of the formula (2), an H in the end product of the formula (1). As a result, the meaning of the radicals $R^1$ to $R^5$ in the starting material of the formula (2), in departure from the meaning originally mentioned in formula (1), can come about.

The process of the invention has a number of advantages in comparison to the processes of the prior art. Firstly, the workup of the resulting reaction mixture proves to be without problems, since only the organic phase must be separated off from the aqueous phase containing the product of value. This avoids a complicated separation of the product of value, for example 2,3,4,5-tetrafluorobenzoic acid, from an amine used as solvent or from a mixture containing an amine and a solvent. The amine obtained by simple phase separation or the mixture containing an amine and a solvent can be reused in the decarboxylation reaction directly or, if appropriate, after purification.

The process of the invention can be carried out at relatively low temperatures (see also Example 2) with relatively short reaction times in a number of cases, for example in the preparation of 2,3,4,5-tetrafluorobenzoic acid. Furthermore, the process of the invention permits a pH range to be employed where corrosion problems are either of only minor importance or are no longer present at all.

A further advantage of the process of the invention is that it is not necessary to use pure starting materials, but crude starting materials, as are sometimes produced, for example, in their preparation, can be used. Obviously, starting materials of this type always, to a certain extent, contain minor components, for example water-soluble salts.

A process variant is that a compound of the formula (2) is used, in which $R^1$, $R^2$, $R^3$, $R^4$ and $R^5$ are identical or different and are COOH, H, F, Cl, OH or an alkoxy radical of 1 to 4 carbon atoms, in particular are identical or different and are COOH, H, F, OH or an alkoxy radical having 1 to 4 carbon atoms. Compounds of the formula (2), in which 0 to 2 of the radicals $R^1$ to $R^5$ are COOH, but also compounds of the formula (2), in which $R^1$ or $R^5$ is COOH, are of particular interest.

As already mentioned at the outset, the process of the invention also relates to the preparation of fluorinated compounds. In this case, usually, a compound of the formula (2) is used, in which one to four of the radicals $R^1$ to $R^5$, in particular two to four of the radicals $R^1$ to $R^5$, preferably two or three of the radicals $R^1$ to $R^5$, are F.

In a number of cases, a compound of the formula (2) is used in which one of the radicals $R^1$ to $R^5$ is OH or an alkoxy group having 1 to 4 carbon atoms, in particular OH.

An aqueous solution can be used in the reaction which contains the starting product in relatively low concentration or else in relatively high concentration. Usually, an aqueous solution is used which contains 1 to 50, in particular 10 to 30, preferably 15 to 25, % by weight of the compound of the formula (2) and, if appropriate, other water-soluble salts or water-soluble compounds, for example in an amount of 0.1 to 60, in particular 20 to 40, % by weight.

Examples of compounds of the formula (2) which may be mentioned, without a claim as to completeness, are: benzoic acids, phthalic acids, isophthalic acids, terephthalic acids, each of which may be chlorinated, brominated or fluorinated, for example 2,3,5-trifluorobenzoic acid, 2,3,4,5-tetrafluorobenzoic acid, 2,3,4,5-tetrachlorobenzoic acid, 3,5-dichlorophthalic acid, 3,6-dichlorophthalic acid, 4,5-dichlorophthalic acid, 3,5-difluorophthalic acid, 3,6-difluorophthalic acid, 4,5-difluorophthalic acid, 3,4,5-trifluorophthalic acid, 3,4,6-trifluorophthalic acid, 2,4,5-trifluoroisophthalic acid, difluoro- and trifluorophthalic acids and -isophthalic acids, in which F can be exchanged for OH, $OCH_3$, $OC_2H_5$, $CF_3$ or $NH_2$, for example 4-hydroxy-3,5,6-trifluorophthalic acid, 4-methoxy-3,5,6-trifluorophthalic acid, 4-ethoxy-3,5,6-trifluorophthalic acid, 4-trifluoromethyl-3,5,6-trifluorophthalic acid, 4-amino-3,5,6-trifluorophthalic acid and 4-dimethylamino-3,5,6-trifluorophthalic acid, in addition trifluoroterephthalic acids, trichloroterephthalic acids, tribromoterephthalic acids, 2,5-dichloroterephthalic acid, 2,5-difluoroterephthalic acid, 2,5-dibromoterephthalic acid, 3,5-dichloroterephthalic acid, 3,5-difluoroterephthalic acid, 3,5-dibromoterephthalic acid and tetrachlorinated phthalic acids, such as tetrafluorophthalic acid, tetrachlorophthalic acid, tetrabromophthalic acid, tetrafluoroisophthalic acid, tetrafluoroterephthalic acid, tetrachloroterephthalic acid and tetrabromoterephthalic acid.

Compounds of the abovementioned type may also be used in which F can be exchanged for OH, $OCH_3$, $OC_2H_5$, $CF_3$ or $NH_2$.

The water-insoluble amine can be used in comparatively small amounts, but also in relatively high amounts. Usually, 0.001 to 50, in particular 0.01 to 2, preferably 0.05 to 1, particularly preferably 0.1 to 0.5, mol of the water-insoluble amine is used per mole of the compound of the formula (2).

The term water-insoluble amine is taken to mean those amines which either dissolve in water only to a slight extent or do not dissolve at all. Usually, the water-insoluble amine used is an alkylamine having 6 to 30 carbon atoms, a dialkylamine having 6 to 30 carbon atoms per alkyl radical, a trialkylamine having 4 to 30 carbon atoms per alkyl radical, a N-containing heterocyclic compound or a mixture of the abovementioned substances, in particular an alkylamine having 8 to 20 carbon atoms in the alkyl radical, a dialkylamine having 8 to 20 carbon atoms per alkyl radical, a trialkylamine having 6 to 20 carbon atoms per alkyl radical, an optionally alkylated quinoline or pyridine, for example collidine, lutidine or picoline or a mixture of the abovementioned substances, preferably a trialkylamine having 6 to 20, in particular 6 to 14, preferably 8 to 12, carbon atoms per alkyl radical or a mixture of these trialkylamines.

Without making a claim as to completeness, examples of suitable amines which may be mentioned are: n-hexylamine, isohexylamine, n-heptylamine, isoheptylamine, n-octylamine, isooctylamine, n-nonylamine, isononylamine, n-decylamine, isodecylamine, n-dodecylamine, isododecylamine, n-hexadecylamine, isohexadecylamine, di-n-hexyleumine, diisohexylamine, di-n-heptylamine, diisoheptylamine, di-n-octylamine, diisooctylamine, di-n-nonylamine, diisononylamine, di-n-decylamine, diisodecylamine, di-n-dodecylamine, diisododecylamine, di-n-hexadecylamine, diisohexadecylamine, tri-n-hexylamine, triisohexylamine, tri-n-heptylamine, triisoheptylamine, tri-n-octylamine, triisooctylamine, tri-n-decylamine, triisodecylamine, tri-n-dodecylamine, triisododecylamine, trialkylamines having straight-chain and/or branched chains having 6 to 14 carbon atoms, pyridine, α-picoline, β-picoline, γ-picoline, 2,4-dimethylpyridine (α,γ-lutidine), 2,6-di-tert-butylpyridine, 2,4,6-trimethylpyridine (collidine), triethylpyridine, quinoline, methylquinolines, ethylquinolines, mixed amines such as butyldihexylamine, dioctyldecylamine, hexyldioctylamine, dihexyloctylamine, diheptyloctylamine, didecyloctylamine, didodecyloctylamine, didodecyldecylamine, didecyldodecylamine, dioctyldodecylamine, dinonyloctylamine, dinonyldecylamine, dinonyldodecylamine.

In general, any mixtures of the abovementioned water-insoluble amines may be used, in particular mixtures of various alkyl- dialkyl- and trialkylamines, preferably mixtures of various trialkylamines having 6 to 14, in particular 8 to 12, carbon atoms.

The reaction can be carried out in the presence or absence of a water-insoluble solvent inert under the reaction conditions. Usually, the inert solvent is used in an amount of 1 to 200, in particular 2 to 50, preferably 5 to 20, % by volume, based on the aqueous solution.

The inert solvent shall, firstly, be insoluble in water, secondly, permit good phase separation at the end of the reaction and, thirdly, dissolve the water-insoluble amine.

Suitable inert solvents are halogenated or nonhalogenated aliphatic hydrocarbons, halogenated or nonhalogenated aromatic hydrocarbons or ethers, in particular chlorinated or nonchlorinated aromatic hydrocarbons, preferably chlorinated or nonchlorinated benzenes. Without making a claim as to completeness, examples of inert solvents which may be mentioned are toluene, o-xylene, m-xylene, p-xylene, mixtures of isomeric xylenes, diphenyl ether, diphenylmethane, biphenyl, o-chlorotoluene, m-chlorotoluene, p-chlorotoluene, o-dichlorobenzene, m-dichlorobenzene, p-dichlorobenzene.

However, any mixtures of the abovementioned solvents may also be used as inert solvent.

As mentioned at the outset, the reaction may be carried out in the presence or absence of a conventional decarboxylation catalyst. A suitable decarboxylation catalyst is copper, a copper(I) compound or a copper(II) compound, for example copper(I) oxide, copper(II) oxide, copper(I) sulfate, copper (II) sulfate, copper (I) chloride, copper (II) chloride, copper (I) fluoride, copper (II) fluoride, copper carbonate, copper (I) hydroxide, copper(II) hydroxide, preferably copper(I) oxide and copper(II) oxide. Any mixtures of the abovementioned substances may also be used.

Usually, the decarboxylation catalyst is used in an amount of 0.1 to 10, in particular 0.5 to 3, mol %, based on the compound of the formula (2).

As already mentioned, the decarboxylation may be carried out in a relatively broad pH range, that is from pH 3 to pH 9.

In a number of cases, the decarboxylation may be carried out highly successfully at a pH of 3.5 to 8, in particular at a pH of 4 to 7, preferably 5 to 7.

In many cases it has proved to be sufficient to carry out the decarboxylation at a temperature of 80 to 180, in particular 90 to 160, °C.

However, the reaction temperature to be employed for the decarboxylation also depends to a certain extent on the type of the particular decarboxylation. If a compound of the formula (2) is used which contains in total two or more COOH radicals, and only one COOH group is eliminated, this decarboxylation may be carried out in the absence of the decarboxylation catalyst at relatively low temperatures. If, in contrast, it is intended to eliminate two or more COOH groups from the abovementioned compound of the formula (2), it is advisable to carry out the reaction either from the beginning at relatively high temperatures, for example at at least 120° C., in particular at least 130° C., preferably at least 140° C. and preferably in the presence of the decarboxylation catalyst, or else to eliminate the first of the COOH groups at relatively low temperature and in the absence of the decarboxylation catalyst then to eliminate the further COOH groups as described above, at higher temperatures and preferably in the presence of the decarboxylation catalyst.

The present process also includes, in particular, the following variant, which comprises carrying out the decarboxylation at a temperature of 80 to 130, in particular 85 to 125, preferably 90 to 120, °C. of a compound of the formula (2), in which one or two of the radicals $R^1$ to $R^5$ or the radical $R^1$ or the radical $R^5$ are COOH, to give a compound of the formula (1), in which one or two of the radicals $R^1$ to $R^5$ or the radical $R^1$ or the radical $R^5$ are COOH. This variant applies in particular to the case when only one COOH group is to be eliminated from the compound of the formula (2) which contains in total two or more COOH groups.

The process may be carried out at reduced pressure, atmospheric pressure or superatmospheric pressure.

The examples below describe the invention in more detail, without restricting it thereto.

EXPERIMENTAL PART

Example 1

Preparation of 3-hydroxy-2,4,5-trifluorobenzoic acid 450.3 g of a strongly alkaline, aqueous solution which contains 41.8 g (0.177 mol) of 4-hydroxy-3,5,6-trifluorophthalic acid in the form of the corresponding alkali metal salts are admixed with 12.6 g of a mixture of various aliphatic trialkylamines each having 6 to 14 carbon atoms in the alkyl radical (Hostarex A 327; a commercial product of Hoechst AG) and the solution is adjusted to pH 5 with in total 166.8 g of a 30% strength aqueous hydrochloric acid and then heated over a period of 6 hours at 105° C. with stirring. The pH changes as a result of the decarboxylation and is appropriately corrected (adjusted to pH 5) after one hour by addition of 23.4 g of 30% strength aqueous hydrochloric acid and after 3 hours by addition of 15.9 g of 30% strength aqueous hydrochloric acid.

The solution is then cooled and a pH of 8 is set for further processing. The water phase (601 g) contains 31.3 g (91.3% of theory) of 3-hydroxy-2,4,5-trifluorobenzoic acid (determined by calibrated HPLC).

If it is intended to isolate 3-hydroxy-2,4,5-trifluorobenzoic acid, the phases are separated after the decarboxylation, the aqueous phase is adjusted to a pH of 1 to 2 and is extracted continuously, for example with methyl tert-butyl ether or butyl acetate. From the organic phase, after drying and filtering and removing the solvent, a solid residue is obtained from which pure 3-hydroxy-2,4,5-trifluorobenzoic acid is obtained by recrystallization.

Example 1a

Preparation of 3-hydroxy-2,4,5-trifluorobenzoic acid

The procedure as described in Example 1 is followed, but only 9 g of a mixture of various aliphatic trialkylamines each having 6 to 14 carbon atoms in the alkyl radical (Hostarex A 327; a commercial product of Hoechst AG) and 518 g of an aqueous solution which contains 29.8 g (0.126 mol) of 4-hydroxy-3,5,6-trifluorophthalic acid in the form of corresponding alkali metal salts are used and, with addition of in total 158.3 g of 30% strength aqueous hydrochloric acid, likewise in 6 hours, 23.25 g (95.9% of theory) of 3-hydroxy-2,4,5-trifluorobenzoic acid are obtained.

If the procedure is followed as specified, but 30 ml of xylene or 50 ml of diphenylmethane are added at the beginning of the reaction or after completion of the reaction, essentially the same results are obtained.

The reaction can also be carried out at a temperature from 85° C., instead of at 105° C., but a prolongation of the reaction time must be accepted, however. A reaction at 90° C. requires, for example, a reaction time of 24 hours, a reaction at 95°to 100° C. only requires a reaction time of 9 hours.

If the reaction is carried out at a pH of 4 or 8, the reaction time likewise lengthens. However, if the reaction is carried out as described above at pH 5.5 to 6, the reaction is completed as early as after 4 to 5 hours at a reaction temperature of 100° to 103° C.

If it is intended to isolate 3-hydroxy-2,4,5-trifluorobenzoic acid, the phases are separated after the decarboxylation, the aqueous phase is adjusted to a pH of 1 to 2 and extracted continuously, for example with methyl tert-butyl ether or butyl acetate. From the organic phase, after drying and filtering and removing the solvent, a solid residue is obtained, from which pure 3-hydroxy-2,4,5-trifluorobenzoic acid is obtained by recrystallization.

Example 2

Preparation of 2,3,4,5-tetrafluorobenzoic acid 55.3 g of a brown, aqueous solution from alkaline hydrolysis which contains 64.5 g (0.271 mol) of 3,4,5,6-tetrafluorophthalic acid are admixed with 50 g of a heat-transport oil which contains alkyl-substituted aromatics as principal constituents. 30 g of a mixture of trialkylamines having 6 to 10 carbon atoms (Hostarex A 324; a commercial product of Hoechst AG) are added and the pH is adjusted to pH 6 to 7 by addition of 55 g of 96% strength sulfuric acid. The mixture is heated over a period of 9 hours to 110° C. with vigorous stirring. Because of the high salt content of the aqueous solution, this temperature corresponds to the reflux temperature. The progress of the reaction is determined by means of HPLC. A mixture is obtained which contains 48.4 g (92% of theory) of 2,3,4,5-tetrafluorobenzoic acid. The mixture can be further processed directly.

To purify 2,3,4,5-tetrafluorobenzoic acid, the organic phase is separated from the aqueous phase, a pH of 1 to 2 is set by addition of acid, and the precipitated 2,3,4,5-tetrafluorobenzoic acid is filtered off. Further purification can be performed either by recrystallization or by fractional distillation.

Example 3

Preparation of methoxytrifluorobenzoic acid 274 g of an aqueous, alkaline solution, which contains 25 g (0.1 mol) of 4-methoxy-3,5,6-trifluorophthalic acid in the form of its alkali metal salts, are admixed with 10 g of trioctylamine and adjusted to pH 7 at a temperature of 107° C. by addition of 62% strength hydrobromic acid. The mixture is allowed to react at this temperature for 14 hours with stirring, the pH being adjusted to the specified value of 7 by addition of hydrobromic acid from time to time.

The progress of the reaction is followed by HPLC. The reaction is completed after the course of a reaction time of 14 hours, this also being recognizable by the termination of gas evolution. The mixture is cooled to a temperature of 0° to 5° C. and sulfuric acid is added to a pH of 1 and methoxytrifluorobenzoic acid is then filtered off by suction. After drying, 18.9 g (85 to 92%) of brownish powder (purity approximately 90%) are obtained, which powder can be used as crude product for further processing or is purified by recrystallization.

Example 4

Preparation of trifluorobenzoic acid 22.0 g (0.1 mol) of 3,5,6-trifluorophthalic acid are dissolved in 50 g of water, 5 g of tridecylamine are added and the pH is adjusted to 6.5 by addition of 30% strength aqueous sodium hydroxide solution with stirring. The mixture is then heated over a period of 10 hours to 100° C. and the pH is kept constant at 6.5 by addition of phosphoric acid, after completion of the reaction (monitoring by HPLC) the mixture is cooled to 5° C., acid is added to a pH of 1, the mixture is heated to 40° C. and the organic phase is separated from the aqueous phase. The aqueous phase contains 15.8 g (0.0898 mol; 90%) of trifluorobenzoic acid as an isomeric mixture (determined by calibrated HPLC) and can be further processed directly.

Example 5

Preparation of a mixture of chlorotrifluoro- and dichlorodifluorobenzoic acids

The procedure as specified in Example 4 is followed, but a completely fluorinated product is not used, but a mixture of chlorotrifluorophthalic acids and dichlorodifluorophthalic acids (corresponding to an amount of 30 g), thus obtaining 23.3 g of a mixture of the corresponding chlorotrifluorobenzoic acids and dichlorodifluorobenzoic acids by extraction of the aqueous phase with butyl acetate, separating off the organic phase, drying over $MgSO_4$ and removing the solvent in vacuo.

Example 6

Preparation of 1,2,3,4-tetrafluorobenzene 19.4 g (0.1 mol) of 2,3,4,5-tetrafluorobenzoic acid are dissolved in 40 g of water, 20 g of a mixture of trialkylamines having 6 to 14 carbon atoms (Hostarex A 327; a commercial product of Hoechst AG) and 0.2 g of copper(I) oxide are added and the pH is adjusted to 7 by addition of 30% strength aqueous sodium hydroxide solution. The decarboxylation is carried out in an autoclave at 155° C. within a period of 4 hours, the evolved carbon dioxide at a pressure of 12 bar being depressurized via a pressure cooler and the distillate passing overhead in this case being collected (cold trap −78° C.). After termination of the reaction, the autoclave is cooled and the 1,2,3,4-tetrafluorobenzene is distilled off by steam at 100° C. and 1.5 l of distillate are obtained, which distillate is combined with the distillate collected previously. The combined distillates are extracted by means of dichloromethane, the organic phase is separated off, dried over magnesium sulfate, filtered and the solvent is removed in vacuo. 10.5 g of crude, slightly yellowish 1,2,3,4-tetrafluorobenzene are obtained, which can be brought to a very high purity by fractional distillation.

COMPARISON EXPERIMENT

Preparation of 2,3,4,5-tetrafluorobenzoic acid (decarboxylation of tetrafluorophthalic acid in anhydrous amine solution)

11.6 g (48.7 mmol) of 3,4,5,6-tetrafluorophthalic acid are dissolved in 40 g of a mixture of trialkylamines having 6 to 14 carbon atoms (Hostarex A 327; a commercial product of Hoechst AG). The slightly yellowish clear solution thus obtained is gradually heated (10° C. per hour) to 100° C. At 100° C., however, no gas evolution ($CO_2$ elimination), which is a measure of the progress of the decarboxylation, can be observed. After 2 hours at 100° C., the temperature is increased for 30 minutes to 115° C. and then for 30 minutes to 120° C. Neither at 115° C. nor at 120° C. is gas evolution observed.

Only when a temperature of 125° C. is achieved does a slight gas evolution start. The mixture is allowed to react for a further 4 hours at this temperature, the reaction is finally completed at 140° C. in a period of 1.5 hours and an orange solution is obtained.

For further workup, the amine solution containing 2,3,4,5-tetrafluorobenzoic acid is admixed with 150 g of water, adjusted to pH 13 with 12 g of 35% strength aqueous sodium hydroxide solution and then extracted 5 times, each time with 75 ml of dichloromethane. The remaining aqueous phase is acidified with 14 g of a 30% strength aqueous hydrochloric acid and then extracted 4 times, each time with 50 ml of methyl tert-butyl ether. The aqueous phase is discarded.

The methyl tert-butyl ether phases are combined and the solvent is removed in vacuo. 8.7 g (44.8 mmol) of colorless to slightly yellowish 2,3,4,5-tetrafluorobenzoic acid of melting point 85.2° C. being obtained as residue in the form of powder and lumps.

We claim:

1. A process for the preparation of compounds of the formula

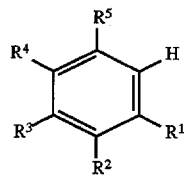 (1)

in which the radicals $R^1$, $R^2$, $R^3$, $R^4$ and $R^5$ are identical or different and are COOH, H, F, Cl, Br, $CF_3$, OH, an alkoxy or alkyl radical having in each case 1 to 4 carbon atoms or a radical $-NR^6R^7$, in which $R^6$ and $R^7$ are identical or different and are H, an alkyl radical having 1 to 4 carbon atoms or a phenyl radical, which comprises dissolving in water a compound of the formula

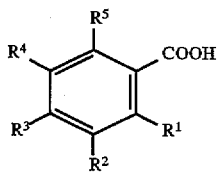 (2)

in which the radicals $R^1$, $R^2$, $R^3$, $R^4$ and $R^5$ are identical or different and have the abovementioned meaning or, in departure therefrom, admixing the aqueous solution with a water-insoluble amine which is inert under the reaction conditions and carrying out the decarboxylation at a pH of 3 to 9 and a temperature of 70° to 210° C. optionally free to be in the presence of a water-insoluble solvent which is inert under the reaction conditions and optionally in the presence of a decarboxylation catalyst.

2. The process as claimed in claim 1, wherein a compound of the formula (2) is used, in which $R^1$, $R^2$, $R^3$, $R^4$ and $R^5$ are identical or different and are COOH, H, F, Cl, OH or an alkoxy radical having 1 to 4 carbon atoms.

3. The process as claimed in claim 1, wherein a compound of the formula (2) is used, in which $R^1$, $R^2$, $R^3$, $R^4$ and $R^5$ are identical or different and are COOH, H, F, OH or an alkoxy radical having 1 to 4 carbon atoms.

4. The process as claimed in claim 1, wherein a compound of the formula (2) is used, in which 0 to 2 of the radicals $R^1$ to $R^5$ are COOH.

5. The process as claimed in claim 1, wherein a compound of the formula (2) is used, in which $R^1$ or $R^5$ is COOH.

6. The process as claimed in claim 1, wherein a compound of the formula (2) is used, in which one to four of the radicals $R^1$ to $R^5$ are F.

7. The process as claimed in claim 1, wherein a compound of the formula (2) is used, in which one of the radicals $R^1$ to $R^5$ is OH or an alkoxy group having 1 to 4 carbon atoms.

8. The process as claimed in claim 1, wherein an aqueous solution is used which contains 1 to 50% by weight of the compound of the formula (2) and, optionally, other water-soluble salts.

9. The process as claimed in claim 1, wherein 0.001 to 50 mol of the water-insoluble amine are used per mole of the compound of the formula (2).

10. The process as claimed in claim 9, wherein 0.01 to 2 mol of the water-insoluble amine are used per mole of the compound of the formula (2).

11. The process as claimed in claim 9, wherein 0.05 to 1 mol of the water-insoluble amine are used per mole of the compound of the formula (2).

12. The process as claimed in claim 9, wherein 0.1 to 0.5 mol of the water-insoluble amine are used per mole of the compound of the formula (2).

13. The process as claimed in claim 1, wherein the water-insoluble amine used is an alkylamine having 6 to 30 carbon atoms, a dialkylamine having 6 to 30 carbon atoms per alkyl radical, a trialkylamine having 4 to 30 carbon atoms per alkyl radical, an N-containing heterocyclic compound or a mixture of the abovementioned amines.

14. The process as claimed in claim 1, wherein the water-insoluble amine used is an alkylamine having 8 to 20 carbon atoms in the alkyl radical, a dialkylamine having 8 to 20 carbon atoms per alkyl radical, a trialkylamine having 6 to 20 carbon atoms per alkyl radical, an optionally alkylated quinoline or pyridine or a mixture of the abovementioned amines.

15. The process as claimed in claim 1, wherein the water-insoluble amine used is a trialkylamine having 6 to 20 carbon atoms per alkyl radical or a mixture of these trialkylamines.

16. The process as claimed in claim 15, wherein the trialkylamine has 6 to 14 carbon atoms per alkyl radical.

17. The process as claimed in claim 1, wherein the inert solvent is used in an amount of 1 to 200% by volume, based on the aqueous solution.

18. The process as claimed in claim 17, wherein the inert solvent is used in an amount of 2 to 50% by volume.

19. The process as claimed in claim 17, wherein the inert solvent is used in an amount of 5 to 20% by volume.

20. The process as claimed in claim 1, wherein as inert solvent, use is made of halogenated or nonhalogenated aliphatic hydrocarbons, halogenated or nonhalogenated aromatic hydrocarbons or ethers or a mixture of these solvents.

21. The process as claimed in claim 20, wherein the inert solvent is a chlorinated or nonchlorinated aromatic hydrocarbon or a chlorinated or nonchlorinated ether or a mixture thereof.

22. The process as claimed in claim 1, wherein the decarboxylation catalyst used is copper, a copper(I) compound, or a copper(II) compound.

23. The process as claimed in claim 1, wherein 0.1 to 10% by weight (mol %) of decarboxylatrion catalyst are used, based on the compound of the formula (2).

24. The process as claimed in claim 23, wherein 0.5 to 3% by weight (mol %) of decarboxylation catalyst are used.

25. The process as claimed in claim 1, wherein the decarboxylation is carried out at a pH of 3.5 to 8.

26. The process as claimed in claim 25, wherein the decarboxylation is carried out at a pH of 4 to 7.

27. The process as claimed in claim 1, wherein the decarboxylation is carried out at a temperature of 80° to 180° C.

28. The process as claimed in claim 27, wherein the decarboxylation is carried out at a temperature of 90° to 160° C.

29. The process as claim in claim 1, wherein the decarboxylation of a compound of the formula (2), in which one or two of the radicals $R^1$ to $R^5$ or $R^1$ or $R^5$ are COOH, to give a compound of the formula (1), in which one or two of the radicals $R^1$ to $R^5$ or $R^1$ or $R^5$ are COOH, is carried out at a temperature of 80° to 130° C.

30. The process as claimed in claim 29, wherein the decarboxylation is carried out at a temperature of 85° to 125° C.

31. The process as claimed in claim 29, wherein the decarboxylation is carried out at a temperature of 90° to 120° C.

32. The process as claimed in claim 1, wherein an aqueous solution is used which contains 10 to 30% by weight of the compound of the formula (2) and, optionally, other water-soluble salts.

* * * * *